United States Patent [19]

Zecher et al.

[11] 4,246,393

[45] Jan. 20, 1981

[54] PROCESS FOR THE PREPARATION OF POLY(THIO)HYDANTOINS

[75] Inventors: Wilfried Zecher, Leverkusen; Jürgen Lewalter, Odenthal; Rudolf Merten; Willi Dünwald, both of Leverkusen, all of Fed. Rep. of Germany

[73] Assignee: Bayer Aktiengesellschaft, Leverkusen, Fed. Rep. of Germany

[21] Appl. No.: 958,941

[22] Filed: Nov. 8, 1978

[30] Foreign Application Priority Data

Dec. 29, 1977 [DE] Fed. Rep. of Germany ....... 2758569

[51] Int. Cl.$^3$ .................... C08G 73/06; C07D 233/78; C09D 3/49; C09J 3/16
[52] U.S. Cl. ........................................ 528/75; 528/45; 528/73; 548/309; 548/310; 548/311; 548/313; 546/210; 544/130; 544/139
[58] Field of Search ............................. 528/73, 75, 45

[56] References Cited

U.S. PATENT DOCUMENTS

| 3,549,599 | 12/1970 | Merten | 528/75 |
| 3,705,874 | 12/1972 | Merten et al. | 528/75 |
| 3,817,926 | 6/1974 | Pauze | 528/75 |
| 4,169,931 | 10/1979 | Rottmaier et al. | 528/75 |

*Primary Examiner*—H. S. Cockeram
*Attorney, Agent, or Firm*—Connolly and Hutz

[57] ABSTRACT

A process for the preparation of a poly(thio)hydantoin, which comprises reacting an organic isocyanate or isothiocyanate having two or more isocyanate or isothiocyanate moieties with an unsaturated dicarboxylic acid of the formula:

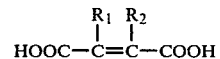

at a temperature of from $-20°$ C. to $+500°$ C., wherein $R_1$ and $R_2$ are hydrogen, halogen, substituted or unsubstituted aliphatic, aliphatic-aromatic, aromatic or heterocyclic.

6 Claims, No Drawings

PROCESS FOR THE PREPARATION OF POLY(THIO)HYDANTOINS

This invention relates to condensates having at least one hydantoin or thiohydantoin ring in the molecule, their preparation from unsaturated carboxylic acids and organic iso(thio)cyanates and their use as a biochemically active substances or for the production of heat-resistant coating compounds.

Processes for the preparation of hydantoins (J. Am. Chem. 45/383) and polyhydantoins (Belgian Pat. No. 678,282) are known. Low molecular weight hydantoins are preferably used in the pharmaceutical field and for plant protection while higher molecular hydantoins are used, for example, for heat-resistant coating compounds (French Pat. No. 1,484,694).

It has surprisingly been found that (thio)hydantoins modified with amide groups are obtained by reacting at temperatures of from $-20°$ C. to $500°$ C., on organic iso(thio)cyanates with unsaturated dicarboxylic acids corresponding to the following general formula (I)

wherein $R_1$ and $R_2$, the same or different, represent hydrogen, halogen, a substituted or unsubstituted aliphatic, aliphatic-aromatic, aromatic or heterocyclic group.

As is well known, the reaction of carboxylic acids with isocyanates takes place with the preferential formation of the corresponding acid anhydrides and ureas, which may continue to react with isocyanates to form complicated and in part polymeric mixtures. However, when at least 2 Val of isocyanate are reacted per mole of unsaturated carboxylic acid, it is surprisingly found that hydantoin ring formation takes place.

The smooth progress of the reaction, which takes place in several stages and also enables polymers to be synthesized, was not to be expected since each stage can proceed to the formation of numerous complicated mixtures of substances, especially in the presence of excess isocyanate. Furthermore, the reaction according to the invention is accompanied only by the liberation of $CO_2$. The liberation of water or alcohol, which occurs in the known processes for the preparation of hydantoins is thus avoided.

The reaction according to the invention may be exemplified by the reaction with monoisocyanates, which is represented by the following equation:

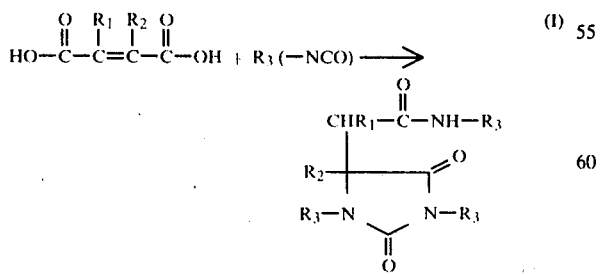

The groups $R_1$ and $R_2$ have the meaning indicated above and $R_3$ will be defined below. Other reaction products, for example hydantoin carboxylic acids, may be formed in addition to the hydantoins modified with amide groups, depending on the reaction conditions.

Iso(thio)cyanates of the following general formula are preferably used:

wherein $R_3$ denotes a substituted or unsubstituted n-valent aliphatic, aliphatic-aromatic, aromatic or heterocyclic group and n represents an integer of from 1 to 4, preferably 1 or 2. Q represents O or S.

The isocyanate may be used in a quantity of from 2 to 12 Val, preferably from 3 to 6 Val, per mol of unsaturated dicarboxylic acid but there is no harm in excess isocyanate being present during the reaction. When $n=1$, monomolecular (thio)hydantoins corresponding to formula (I) are obtained; when n is greater than 1, the products obtained are oligomeric or polymeric (thio)hydantoins with molecular weights of up to 200,000, depending upon the stoichiometric ratios of starting materials. At least 3 Val of a polyfunctional iso(thio)cyanate are used for synthesizing the oligomers or polymers.

According to a preferred embodiment, at least 2 moles, preferably 2.5 to 3 moles, of a diiso(thio)cyanate are used per mole of unsaturated dicarboxylic acid. The polyiso(thio)cyanates thereby obtained have the following structural unit (II):

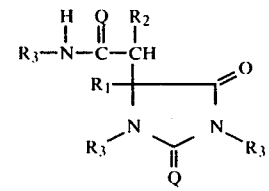

which may be recurring and which may be linked through $R_3$ groups, and which optionally has masked isocyanate end groups. Q represents O or S. The groups $R_1$, $R_2$ and $R_3$ have the meaning indicated above. (Thio)hydantoin iso(thio)cyanates from this series are suitable as components and cross-linking agents, for example for polyesters, polyurethanes, polyhydantoins or polyimides.

The (thio)hydantoins according to the invention may be identified by the characteristic IR bands of (thio)hydantoins. The higher molecular weight (thio)hydantoins dissolved as 30% by weight solutions, e.g. in acetophenone, butyrolactone, cresol or benzoic acid alkyl esters, have solution viscosities at $20°$ C. of from 50 to 200,000 mPa.s, preferably from 500 to 50,000 mPa.s.

As unsaturated dicarboxylic acids compounds corresponding to the general formula (I) are preferably used:

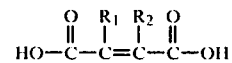

wherein $R_1$ and $R_2$, which may be the same or different, preferably denote hydrogen, halogen, an aliphatic $C_1$-$C_{20}$ group, an aliphatic-aromatic $C_7$-$C_{20}$ group, an aromatic $C_6$-$C_{20}$ group or a heterocyclic group with 5 to 16 ring members and at least one N, O or S atom.

$R_1$ and $R_2$ may represent, for example, hydrogen, fluorine, chlorine, bromine or a methane, ethane, hexane, cyclohexane, propene, benzene, toluene, piperidine, morpholine, or imidazole group, or together they may form a ring having up to 8 ring members.

The unsaturated dicarboxylic acids may also be prepared by the reaction in situ of the corresponding anhydrides with a tertiary alcohol. Cis and trans isomeric structures of the unsaturated dicarboxylic acids may be used, which are obtained by known processes, optionally in situ, e.g. by irradiation, heating or reaction with halogen or bases. $R_1$ and $R_2$ are most preferably hydrogen, i.e. the dicarboxylic acids are the isomeric maleic acid and fumaric acid.

The organic iso(thio)cyanates used may be mono- and/or polyiso(thio)cyanates.

The monoisocyanates used for the invention are aliphatic or aromatic compounds having one isocyanate group in the molecule, optionally substituted by hetero atoms, e.g. alkyl isocyanates such as ethyl, methyl, butyl, dodecyl or stearyl isocyanate; aromatic substituted or unsubstituted monoisocyanates such as phenyl, tolyl, isopropylphenyl- or nonylphenyl-isocyanate; nitro-, alkoxy-, aroxy-, chloro-, dichloro-, trichloro-, tetrachloro-, pentachloro-, benzyl- or bromophenyl isocyanate; isocyanatobenzoic, -phthalic or -isophthalic acid ester; isocyanatobenzonitrile; cycloaliphatic isocyanates such as cyclohexyl isocyanate; or unsaturated isocyanates such as allyl, oleyl, or cyclohexenyl isocyanate.

The isocyanates used as starting components according to the invention may also be aliphatic, cycloaliphatic, araliphatic, aromatic or heterocyclic polyisocyanates (see Annalen 562, Pages 75 to 136), for example ethylene diisocyanate, 1,4-tetramethylene diisocyanate, 1,6-hexamethylene diisocyanate, 1,12-dodecane diisocyanate, cyclobutane-1,3-diisocyanate, cyclohexane-1,3- and 1,4-diisocyanate and any mixtures of these isomers, 1-isocyanato-3,3,5-trimethyl-5-isocyanato-methyl-cyclohexane (German Auslegeschrift No. 1,202,785), 2,4- and 2,6-hexahydrotoluene diisocyanate and any mixtures of these isomers, hexahydro-1,3- and/or 1,4-phenylene diisocyanate, perhydro-2,4'- and/or -4,4'-diphenyl methane diisocyanate, 1,3- and 1,4-phenylene diisocyanate, 2,4- and 2,6-toluylene diisocyanate and any mixtures of these isomers, diphenyl methane-2,4'- and/or -4,4'-diisocyanate, naphthylene-1,5-diisocyanate, triphenylmethane-4,4',4"-triisocyanate, polyphenyl-polymethylene-polyisocyanates which may be obtained by aniline-formaldehyde condensation followed by phosgenation and which have been described e.g. in British Pat. Nos. 874,430 and 848,671, perchlorinated aryl polyisocyanates, e.g. those described in German Auslegsschrift No. 1,157,601, polyisocyanates with carbodiimide groups as described in German Pat. No. 1,092,007, the diisocyanates described in U.S. Pat. No. 3,492,330, polyisocyanates with allophanate groups as described e.g. in British Pat. No. 994,890, Belgian Pat. No. 761,626 and published Dutch Pat. Application No. 7,102,524, polyisocyanates with isocyanurate groups as described e.g. in German Pat. Nos. 1,022,789; 1,222,067 and 1,027,394 and in German Offenlegungsschriften Nos. 1,929,034 and 2,004,048, polyisocyanates with urethane groups as described e.g. in Belgian Pat. No. 752,261 or in U.S. Pat. No. 3,394,164, polyisocyanates with acylated urea groups according to German Pat. No. 1,230,778, polyisocyanates with biuret groups as described e.g. in German Pat. No. 1,101,394, British Pat. No. 889,050 and French Pat. No. 7,017,514, polyisocyanates prepared by telomerisation reactions as described e.g. in Belgian Pat. No. 723,640, polyisocyanates with ester groups as described e.g. in British Pat. Nos. 956,474 and 1,072,956, U.S. Pat. No. 3,567,763 and German Pat. No. 1,231,688, and reaction products of the above mentioned isocyanates with acetals according to German Pat. No. 1,072,358.

The distillation residues still containing isocyanate groups from the commercial production of isocyanates may also be used, optionally dissolved in one or more of the above mentioned polyisocyanates. Any mixtures of the above mentioned polyisocyanates may also be used.

Particularly suitable iso(thio)cyanates are those corresponding to the general formula (III):

$$R_3(-NCQ)_n \qquad (III)$$

wherein
Q is O or S;
$R_3$ represents an alkyl group with 2 to 20 C-atoms; an aryl group with 5 to 12 C atoms; a cycloalkyl group with 5 to 12 C-atoms; an alkyl-aryl group with 6 to 20 C-atoms; and an aryl or cycloalkyl group with 5 to 12 C-atoms containing hetero atoms such as N, O or S, all of which may be substituted with halogen or with $C_1-C_{10}$ alkyl groups and/or $C_6-C_{12}$ aryl groups;

n represents an integer of from 1 to 4, preferably 1 to 3, and is most preferably 2. Aliphatic groups having from 2 to 12 C-atoms and aryl groups such as phenyl, tolyl, naphthyl, diphenyl methane and diphenyl ether groups are particularly preferred.

The following are preferably used: commercially readily available mixtures of toluylene diisocyanates, m-phenylene diisocyanate, phosgenated condensates of aniline and formaldehyde which have a polyphenylene-methylene structure, the symmetrical compounds 4,4'-diisocyanatodiphenyl methane, 4,4'-diisocyanatodiphenyl ether, p-phenylene diisocyanate and 4,4'-diisocyanatodipheyl dimethyl methane, as well as isophorone diisocyanate and hexamethylene diisocyanate.

The iso(thio)cyanates may be used in the free form or partly or completely in the form of their derivatives which are obtained by their reaction with compounds containing reactive hydrogen and which react as isocyanate-releasing compounds under the reaction conditions.

The isocyanate-releasing compounds preferably used are addition products of lactams, oximes and CH-acidic compounds as well as the carbamic acid esters obtained from aliphatic and aromatic monohydroxy and polyhydroxy compounds, for example those corresponding to the following general formulae:

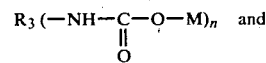

and

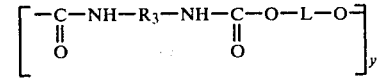

wherein $R_3$ and n have the meaning indicated above, M denotes the organic group of a monohydroxyl compound and L denotes the organic group of a difunctional or trifunctional hydroxyl compound. M and L, which may be identical or different, preferably represent an aliphatic group having 1 to 10 C-atoms, a cycloaliphatic group having 5 to 10 C-atoms, an aliphatic-aromatic group having 7 to 12 C-atoms or an aromatic group having 6 to 12 C-atoms, each of which groups may be further substituted with $C_1-C_{10}$ alkyl groups and/or $C_6$–$C_{12}$ aryl groups; y represents an integer of from 1 to 1,000, preferably from 1 to 100.

Examples include the carbamic acid esters of phenol, isomeric cresols, commercial mixtures thereof and similar aromatic hydroxyl compounds, aliphatic monohydric alcohols such as methanol, ethanol, propanol, isopropanol, butanol, isobutanol, cyclohexanol and allyl alcohol, benzyl alcohol, aliphatic dihydric and polyhydric alcohols such as ethylene glycol and trimethylol propane, and addition products with pyrrolidone-(2), caprolactam, butanone oxime, malonic esters, ethyl acetoacetate and acetophenone.

The isocyanate-releasing compounds may be prepared before they are put into the process or they may be prepared in situ by reaction with the appropriate reactants.

Instead of the above mentioned (poly)isocyanates, the analogous (poly)isothiocyanates may be used as starting materials.

Examples of hydroxy alkyl ethers, which are particularly preferred both as blocking agents and as solvents, include compounds corresponding to the general formula (IV):

$$R_8\text{--}(OR_9)_q\text{--}OH \qquad (IV)$$

wherein $R^8$ represents a $C_1$–$C_{20}$, preferably $C_1$–$C_8$, substituted or unsubstituted aliphatic group; a $C_4$–$C_{10}$, preferably $C_5$–$C_8$ cycloaliphatic group; a $C_7$–$C_{16}$ aliphatic-aromatic group or a $C_6$–$C_{14}$ aromatic group which may be substituted, for example with alkoxy, aroxy or hydroxyl groups; $R^9$ denotes a $C_2$–$C_{20}$ aliphatic group and q represents an integer of from 1 to 100, preferably 1 to 4. The hydroxyalkyl ethers used according to the invention are preferably of the type which contain one hydroxyl group per molecule and in which $R^9$ is a group having two carbon atoms in the chain which may be substituted, for example by alkyl groups, for example methyl-, isopropyl-, cyclohexyl-, benzyl-, phenyl- and methoxyethyl-ethylene glycol- and -propylene glycol- or -diethylene glycol- and -dipropylene glycol-monoethers.

The reaction according to the invention of unsaturated dicarboxyic acids with organic iso(thio)cyanates to form the (thio)-hydantoins or (thio)hydantoin group-containing polyiso(thio)cynates according to the invention may be carried out in solvents which are inert under the reaction conditions or form loose addition compounds which undergo further reactions, or it may be carried out in an excess of one of the reactants.

Suitable solvents, apart from the blocking agents mentioned above, include hydrocarbons, halogenated hydrocarbons, esters, cyclic esters, ketones, ethers, substituted amides and nitriles. The following are specific examples: xylenes, o-dichlorobenzene, acetophenone, cyclohexanone, ethylene glycol butyl ether, diethylene glycol methyl ether, glycol monomethyl ether acetate, δ-butyrolactone, ε-caprolactone, benzoic acid alkyl esters, N-methyl-pyrrolidone, dimethyl formamide, dimethyl acetamide and benzonitrile among others, and mixtures thereof.

To carry out the process according to the invention, the reactants, with or without solvents and/or blocking agents, are maintained at temperatures of from −20° C. to 500° C., preferably from 0° C. to 450° C., for a time which may vary from a few minutes to several hours.

The progress of the reaction may be followed by observing the evolution of $CO_2$ gas and the IR spectrum.

The acidity of acid solvents such as phenols and cresols is sufficient to enable the reaction to be completed within an acceptable time. In inert media or in solvent-free reaction mixtures, carboxylic acids with sufficiently high melting or boiling points, for example, such as acetic acid, benzoic acid, succinic acid, benzodicarboxylic acids, butane tetracarboxylic acid, trimellitic acid or their anhydrides may also be used as catalysts which become chemically fixed in the reaction products. These may be added in quantities of from 0.1 to 40% by Val, preferably from 1 to 10% by Val, based on one Val of iso(thio)cyanate.

The known catalysts of isocyanate chemistry may be used to accelerate the reactions, including bases such as triethylamine, N-methyl morpholine and endoethylene piperazine or acids such as p-toluene sulphonic acid or metals, in particular iron, lead, zinc, tin, copper, cobalt or titanium or compounds thereof, for example titanium tetrabutylate, titanium amino alcohol, iron acetyl acetonate, dibutyl tin laurate, lead acetate or zinc octoate; or phosphorus compounds such as trialkyl phosphine.

It is sometimes advantageous to carry out the reaction in several stages. By controlling the temperature stepwise and adding the isocyanates in several stages, or optionally several different isocyanates, it is possible to control the structure of the products obtained by the process of the invention. Thus, for example, an adduct or condensate may be prepared in a first stage, optionally in a solvent and/or blocking agent, and this adduct or condensate may then be converted into the optionally high molecular condensation product by a reaction at a higher temperature accompanied by cyclisation and/or chain lengthening and/or cross linking, optionally after the addition of latent blocking agents and optionally accompanied by evaporation of the solvent. If this condensation product is subsequently used for coating purposes, it may be applied from a solvent-free melt or from aqueous systems.

It is sometimes advisable to carry out the reaction under an inert protective gas such as $N_2$ or argon.

Lastly, the reaction according to the invention may be carried out either continuously or batchwise, and optionally in autoclaves under pressure in order to obtain higher reaction temperature.

In general, the reaction according to the invention is advantageously carried out using at least 2 Val, preferably 3 to 6 Val, of iso(thio)cyanate per mole of unsaturated dicarboxylic acid.

The degree of polymerisation and the isocyanate content can be varied by the addition of monoisocyanates such as phenyl isocyanate, α-naphthyl isocyanate, isocyanatobenzoic acid ester or isocyanatoacetic acid ester.

The reaction products may be worked up by the usual methods such as crystallization.

According to another method of carrying out the reaction according to the invention, other compounds, for example polybasic amines, polyhydric alcohols such as ethylene glycol, trimethylol propane, glycerol or trihydroxy ethyl isocyanurate and/or polybasic carboxylic acids or their anhydrides such as phthalic acid, isophthalic acid, terephthalic acid, trimellitic acid or butane tetracarboxylic acid and/or other polyisocyanates or polyisocyanate-releasing compounds are also used, optionally in situ, and converted by the usual methods into linear and/or branched chain synthetic resins containing e.g. ester, carbamic ester, amide and/or imide groups, which products are characterized by their high solubility, increased temperature resistance, high elasticity and good heat shock characteristics.

The condensation products according to the invention, and optionally their preliminary stages, may with similar success also be mixed with polyesters, for example formed from phthalic acid/terephthalic acid/isophthalic acid or their esters, ethylene glycol, glycerol/trimethylol propane/trihydroxyethyl isocyanurate; polyethers, for example formed from ethylene oxide and/or bis-(hydroxy-phenyl)-propane and epichlorohydrin; polyurethanes, polyamides, polyimides or polyesters and they may be condensed with these substances or the reaction may be carried out in the presence of these components. In all these cases there are produced modified polymers which, in addition to (thio)hydantoin rings, may contain additional ether, carbamic ester, carboxylic acid ester, amide, imide, ester amide, ester imide, amidoimide and/or esteramidoimide groups.

The proportions in which these additives are used may vary within wide limits but are preferably from 10 to 400% by weight, with respect to the condensate according to the invention.

The low molecular and monomolecular (thio)hydantoins obtainable by the process according to the invention are biochemically active and the poly(thio)hydantoins according to the invention are exceptionally temperature resistant.

Synthetic resins which are modified with the polycondensates according to the invention are distinguished by their improved temperature resistance and improved solubility. The polymers may be used for the manufacture of temperature-resistant adhesives, lacquers, foils, powders and plastics or other synthetic materials and for coating heat-resistant substrates. Their properties may be varied within wide limits by the addition of fillers, pigments and low-molecular and high-molecular components according to the field in which they are to be used.

In the following examples the percentages, proportions and parts are all by weight.

EXAMPLE 1

58 g of fumaric acid and 375 g of 4,4'-diisocyanatodiphenyl methane are introduced into 570 g of butyrolactone. The mixture is then heated to 110° C. and 111 g of n-butanol are added dropwise at this temperature at a rate depending upon the exothermic reaction. The reaction mixture is then stirred for 3 hours at 130° C., 3 hours at 150° C. and 7 hours at 170° C. Condensation to form the hydantoin is accompanied by the liberation of carbon dioxide. A brown, viscous solution of hydantoin isocyanate blocked with butanol is obtained. Its isocyanate content is below 0.5% and the IR spectrum shows the characteristic hydantoin bands at 1720 and 1770 $cm^{-1}$.

To prepare a lacquer solution, 200 g of the reaction products are mixed with 100 g of a polyester of terephthalic acid, ethylene glycol and glycerol. The mixture is diluted with cresol to a solids content of 30% and 0.5% of titanium tetrabutylate is added as catalyst. This solution is used to lacquer a copper wire 0.7 mm in diameter in a wire lacquering machine.

Length of furnace: 4 m
Furnace temperature: 400° C.
Number of passages through furnace: 6

Under these conditions, at a draw-off rate of the wire of 9 meters per minute, a coated wire having a softening temperature of 324° C. and an abrasion resistance of 20 strokes is obtained.

EXAMPLE 2

168 g of a commercial cresol mixture are added dropwise to a solution of 375 g of 4,4'-diisocyanatodiphenyl methane and 58 g of fumaric acid in 570 g of butyrolactone at 120° C. The mixture is then stirred at 130° C., 150° C., 170° C. and 175° C., for 2 hours at each temperature. The hydantoin isocyanate masked with cresol is obtained as a brown solution showing the typical hydantoin bands in the IR spectrum at 1720 and 1775 $cm^{-1}$. The masked isocyanate content is 5.6% and the viscosity $\eta^{25}$ is 360 m Pas.

The reaction product is mixed in a ratio of 1:1 with a polyester of terephthalic acid, ethylene glycol and glycerol and diluted with cresol to a solids content of 30%, and 1.5% of titanium tetrabutylate is added as catalyst. This solution is used to lacquer a copper wire 0.7 mm in diameter as described in Example 1. Under these conditions, an insulated wire having a maximum external elongation of 88% and a softening temperature of 318° C. is obtained at a draw-off rate of 11 meters per minute.

EXAMPLE 3

58 g of fumaric acid are introduced into 600 g of a commercial cresol mixture. 261 g of a mixture of 80 parts of 2,4- and 20 parts of 2,6-tolylene diisocyanate are added in portions at 120° C. The mixture is then stirred for 2 hours at 150° C., 2 hours at 170° C. and 6 hours at 190° C. Condensation to the hydantoin takes place, accompanied by the liberation of carbon dioxide. The hydantoin isocyanate masked with cresol is obtained as a brown, viscous solution containing 6.7% of masked isocyanate. A sample is mixed in proportions by weight of 1:1 with a polyester of isophthalic acid, ethylene glycol and trimethylol propane and diluted to a solids content of about 30% with acetophenone. This lacquer solution is painted over a metal sheet and stoved for 15 minutes at 200° C. and 15 minutes at 300° C. to produce a clear, elastic lacquer film.

EXAMPLE 4

96 g of Solvesso 100 ® (a commercial mixture of alkyl aromatic compounds), 58 g of fumaric acid and 261 g of a mixture of 80 parts of 2,4- and 20 parts of 2,6-tolylene diisocyanate are introduced into a reaction vessel and heated to 100° C. 180 g of diethylene glycol monomethyl ether are then added dropwise at this temperature with cooling. The reaction mixture is then stirred at 120°, 150° and 170° C., for 2 hours at each of these temperatures, and then at 190° C. for 4 hours. Any Solvesso not removed in the course of the reaction is distilled off under vacuum. The reaction product, a hydantoin isocyanate masked with diethylene glycol monomethyl ether, is poured out as a solvent-free melt and solidifies to a yellow-brown resin. The free isocyanate content is less than 0.2%. 200 g of this resin and 200 g of a polyester of terephthalic acid, ethylene glycol and glycerol are used to prepare a 30% solution in cresol, to which 1.5% of titanium tetrabutylate is added as catalyst. This lacquer solution is used to lacquer a copper wire 0.7 mm in diameter under the conditions described in Example 1. A lacquer wire having a softening temperature of 310° C. and an abrasion resistance of 19 strokes is obtained at a draw-off rate of 9 meters per minute.

EXAMPLE 5

70 g of 2,4-tolylene diisocyanate are added dropwise at 110° to 120° C. to a solution of 152 g of a hydantoin isocyanate masked with cresol, which has been prepared according to Example 2, and 31 g of ethylene glycol in 255 g of a commercial cresol mixture. The reaction mixture is then stirred for 30 minutes at 120° C. and 192 g of trimellitic acid anhydride are introduced. The reaction mixture is then stirred at 170, 190, 200 and 205° C. for 2 hours at each of these temperatures. Condensation takes place, accompanied by the elimination of carbon dioxide and water. The reaction product, a polyester imide hydantoin which shows the characteristic bands at 1715 and 1775 cm$^{-1}$ in the IR spectrum, is diluted with 150 g of a mixture of equal parts of phenol and cresol. The viscosity $\eta^{25}$ is 13,000 m Pas. A sample is diluted with cresol to 30% by weight and equal parts, based on the solids content, of a polyester of terephthalic acid, ethylene glycol and glycerol are added, together with 1.5% of titanium tetrabutylate as catalyst. The resulting lacquer solution is painted on a glass plate and stoved for 15 minutes at 200° C. followed by 15 minutes at 300° C. to form a clear, elastic lacquer film.

EXAMPLE 6

261 g of a mixture of 80 parts of 2,4- and 20 parts of 2,6- tolylene diisocyanate are introduced dropwise with cooling into 58 g of fumaric acid in 600 g of cresol at 120° C. The reaction mixture is then stirred at 190° C. for 8 hours. It is then cooled to 120° C. and 85 g of ethylene glycol, 130 g of 2,4-tolylene diisocyanate and 524 g of trimellitic acid anhydride are added at this temperature. The reaction mixture is then heated and stirred at 190°, 200° and 210° C., for 2 hours at each of these temperatures. The reaction product, a polyesterimide hydantoin, is diluted to an approximately 40% solution with 650 g of cresol. The viscosity $\eta^{25}$ of a 15% solution in cresol is 400 m Pas. A sample of the reaction product is painted on a metal sheet and stoved for 15 minutes at 200° C. and then for 15 minutes at 300° C. to form a hard, clear lacquer film.

EXAMPLE 7

An isocyanate-free solution previously prepared from 232.2 g of maleic acid, 562.8 g of Carbitol (diethylene glycol monoethyl ether) and 18 g of ε-caprolactam by the addition of 222 g of isophorone diisocyanate (with liberation of $CO_2$) at 30°–70° C. under nitrogen, is added by portions at 50°–150° C. under nitrogen to 1000.8 g of 4,4'-diisocyanatodiphenyl methane. The reaction mixture is homogenized for 1 hour at 150° C. and finally condensed at 200°–220° C. (reflux) for about 4 hours.

The blackish brown, homogenous resin obtained shows the typical IR bands of hydantoin and has a latent isocyanate content of about 9.0% and a viscosity of about 20,000 cP$_{20°\ C.}$ in a 70% Carbitol solution.

EXAMPLE 8

A mixture of 116.1 g of fumaric acid, 10 g of ε-caprolactam and 340 g of benzyl alcohol is added at 30°–70° C. under nitrogen to 522 g of tolylene diisocyanate (mixture of 2,4:2,6 isomers in ratio of 80:20) and the mixture is then heated through 100°, 120° and 150° C. to 160°–175° C. and condensed for 1 hour at 200° C. after the evolution of $CO_2$ has ceased.

The blackish brown, brittle resin obtained shows the typical IR bands of hydantoin, has a viscosity of about 250 cp$_{150°\ C.}$ and has a latent isocyanate content of about 13% by weight.

EXAMPLE 9

A mixture of 11.6 g of maleic acid, 1 g of ε-caprolactam, 42 g of Carbitol, 0.05 g of Dabco ® Endoethylenpiperazin and 0.05 g of iodine previously briefly heated to 140°–150° C. is mixed with 75.0 g of 4,4'-diisocyanatodiphenyl methane at 30°–70° C. under nitrogen, and the resulting mixture if homogenized and heated through 100°/120°/150° C. to 160°–175° C. When the evolution of $CO_2$ has ceased, the mixture is briefly heated to 190°–210° C.

The isocyanate-free melt is then diluted with 970 g of xylenol L ® at 120°–100° C. 520 g of a polyester of 5.7 moles of dimethyl terephthalate, 1.9 moles of tris-(2-hydroxyethyl)-isocyanurate, 0.6 mole of trimethylol propane, 10.0 mole of ethylene glycol, 300 g of Solvesso, 1.0 g of lead acetate and 1.0 g of butyl titanate, having a hydroxyl group content of about 4.5% by weight, are added and the mixture is homogenized at 180°–200° C. for about half an hour. 6.5 g of titanium tetrabutylate are then added at 100°–80° C.

The viscosity of the approximately 40% lacquer solution is about 1700 cp$_{20°\ C.}$.

Copper wires 0.7 mm in diameter which have been coated with this solution in a 4 meter furnace at 9 meters per minute have a softening temperature of about 315°–320° C., a heat shock resistance of at least 220° C. and a heat endurance at 200° C. of about 14 days.

EXAMPLE 10

19.3 g of maleic acid and 0.2 g of iodine in 500 g of m-cresol 70 are heated to 140°–150° C. under nitrogen for approximately 1 minute. 298.9 g of N,N'-bis-(2-methoxycarbonyl propyl-2)-4,4'-diamino-diphenyl methane are then added at 50° C. and then, starting at a temperature of 30°–45° C., rapidly mixed with a solution of 250.2 g of 4,4'-diisocyanato diphenyl methane is 200 g of toluene. 0.5 g of Dabco ® is added after about 3 hours at 25° C.–35° C. The reaction mixture is heated through 100°/120°/140°/160° to 175° C. and $CO_2$ and methanol/toluene are removed at the same time. The mixture is finally condensed at 200° C. for about 6 hours. As the viscosity progressively rises, the reaction mixture is diluted with a total of 680 g of m-cresol 70 ® and homogenized for 1 hour at 200° C. The approximately 30% lacquer solution has a viscosity of 4,750 cP$_{20°\ C.}$.

The binder remaining behind after methanol precipitation shows the characteristic hydantoin bands in the IR spectrum.

A lacquered 0.7 mm copper wire produced by lacquer coating in a 4 meter furnace at 9 meters per minute has a softening temperature above 380° C., a heat shock resistance of above 260° C. and a heat endurance of at least 14 days at 200° C.

EXAMPLE 11

77.8 g of maleic acid, 16.6 g of isophthalic acid and 0.3 g of iodine in 500 g of γ-butyrolactone are heated to 140°–150° C. under nitrogen for about 1 minute. 298.9 g of N,N'-bis-(2-methoxy carbonyl propyl-2)-4,4'-diaminodiphenyl methane are then added at 30° C. A solution of 663.0 g of 4,4'-diisocyanatodiphenyl methane in 200 g of toluene is finally added all at once at 20°

C. and the mixture is stirred. After about 3 hours at 25° C.-35° C., 0.5 g of Dabco ® is added and the reaction mixture is slowly heated through 60°/80°/120°/150° C. to 175° C. and $CO_2$, methanol and toluene are removed at the same time. When the liberation of $CO_2$ has ceased 230.5 g of trimellitic acid anhydride and 66.5 g of isophthalic acid are added at 70° C. and the mixture is homogenized and finally condensed at 200° C. for about 5 hours. 97.7 g of dimethyl terephthalate, 184.2 g of glycerol and 1.0 g of butyl titanate are then added at 120° C. and the reaction mixture is heated through 140°/150° C. to 200°-220° C. and maintained at this temperature for about 6 hours. The reaction mixture is finally condensed at 200°-210° C. under vacuum for about 1 hour.

The reaction mixture is finally diluted with 955 g of ε-caprolactone at 150°-120° C. and a solution of 14 g of titanium tetrabutylate in 28 g of acetyl acetone is added. The reaction mixture is then homogenized for about 1 hour at 120°-100° C.

The approximately 50% lacquer solution has a viscosity of 17,300 $cP_{20° C.}$.

A lacquered copper wire 0.7 mm in diameter lacquered in a 4 meter furnace at 9 meters per minute has a softening temperature of above 330° C. (DIN 46 455), a heat shock resistance of above 260° C., a heat endurance of above 7 days at 200° C. (DIN 46 453), an abrasion resistance (DIN 46 453) of 95 double strokes, a lacquer film hardness of 5 H(DIN 46 453), an electrical insulation value of 9 KV and good chemical resistance.

EXAMPLE 12

76.8 g of trimellitic acid anhydride and 8.3 g of isophthalic acid are dissolved in 500 g of m-cresol 70 ® under nitrogen with heating. 298.9 g of N,N'-bis-(2-methoxycarbonyl propyl-2)-4,4'-diaminodiphenyl methane are then added at room temperature. A solution of 725.6 g of 4,4'-diisocyanatodiphenyl methane in 200 g of toluene are added, starting at 30°-45° C. After 3 hours at room temperature, 307.4 g of trimellitic acid anhydride and 69.6 g of fumaric acid are added. The mixture is homogenized and 0.5 g of Dabco ® is added. The temperature is then slowly raised by heating 70°/100°/120° to 150° C. and when evolution of $CO_2$ has abated the mixture is condensed for about 5 hours at 200° C.

97.7 g of dimethyl terephthalate, 186 g of glycol and 1.0 g of butyl titanate are finally added at 120°-100° C. and the mixture is heated through 140°/150° C. to 200° C. After about 4 hours at 200°-220° C., condensation is carried out under vacuum at 200°-210° C. until the lacquer solution diluted to a solids content of 50% with benzyl alcohol has a viscosity of about 2,700 $cP_{20° C.}$ When a deep drawn metal sheet coated with this lacquer solution is stoved at 250° C. for 15 minutes and than at 300° C. for 10 minutes, it is covered with a firmly adhering, highly elastic lacquer film. The coatings have a pencil hardness of 5 H. The lacquer may also be applied to glass, for example, to form a film in known manner. Foils produced in this way have good mechanical properties and high heat resistance, with a melting point above 330° C.

EXAMPLE 13

116.1 g of fumaric acid and 16.6 g of isophthalic acid in 500 g of γ-butyrolactone are heated to 100° C. for about 1 minute under nitrogen and then mixed with a solution of 775.6 g of 4,4'-diisocyanatodiphenyl methane in 200 g of toluene at 30° C. Stirring is then continued for about 1 hour. After the addition of 0.5 g of Dabco ®, the reaction mixture is slowly heated to about 150° C. through 70° and 100° C. When the evolution of $CO_2$ has ceased, the reaction mixture is cooled to about 70° C. and 574.4 g of trimellitic acid anhydride are added. The mixture is then again heated, this time to about 175° C. through 70°, 100° and 150° C. and condensed at 200° C. for about 5 hours. 124.2 g of glycol, 92.1 g of glycerol and 1.0 g of butyl titanate are then added at 120°-100° C. and the mixture is heated to 200° C. through 140°/150° C. After about 4 hours at 200°-220° C., the reaction mixture is condensed under vacuum at 200° to 210° C. until the resulting lacquer solution diluted to 50% with benzyl alcohol has a viscosity of about 67,000 $cP_{20° C.}$.

A deep drawn metal sheet coated with this lacquer solution analogously to Example 12 is found to have a firmly adhering, elastic lacquer film with great surface hardness.

EXAMPLE 14

35.7 g of phenyl isocyanate are mixed with 70.0 g of m-cresol. 11.6 g of maleic acid are added under nitrogen in the course of evolution of $CO_2$ at temperatures starting from 10° C. to below 40° C. 0.2 g of iodine is added, stirring is continued for about 1 hour at 70° C., 0.1 g of Dabco ® is then added, the mixture is slowly heated to 170° C. through 100°/130°/150° C. and the temperature is finally raised to the reflux temperature until all the isocyanate groups have been used up. The product is worked up by distilling off the cresol under vacuum and recrystallizing the residue from alcohol/petroleum ether. About 5 g of colourless crystals melting at 203° C. to 205° C. are obtained. The crystals show the typical hydantoin bands at 1710 and 1755 $cm^{-1}$ in the IR absorption spectrum and an amide band at 1650 $cm^{-1}$.

The analysis calculated on the basis of 1,3-diphenyl-5-(N-phenylaminocarbonyl methyl)-hydantoin gives the following results for $C_{23}H_{16}N_3O_3$ (385.4);

| Calculated: | C | 71.7 | H | 5.0 | N | 10.9 |
|---|---|---|---|---|---|---|
| Found: | | 72.0 | | 5.1 | | 10.4 |

EXAMPLE 15

1392 g of tolylene diisocyanate (mixture of 2,4:2,6 isomers in ratio of 80:20) are mixed with 116.1 g of fumaric acid at room temperature under nitrogen. 0.1 g of triethylene diamine is added and the reaction mixture is slowly heated to 175° C., at a rate depending upon the evolution of $CO_2$. Stirring is then continued for about 3 hours at 175° C., until the evolution of $CO_2$ ceases.

A dark brown oil is obtained which shows the characteristic hydantoin bands in addition to the isocyanate bands in the IR spectrum. The isocyanate content of the oil is about 31.0% by weight.

EXAMPLE 16

24.5 g of maleic acid anhydride and 18.5 g of tertiary butanol are stirred under nitrogen until the evolution of isobutylene ceases (about 1 hour). The resulting unctuous substance is then dissolved in 150 g of γ-butyrolactone, homogenized and finally stirred up with 0.1 g of iodine. Stirring is then continued for about 1 hour at 70° C. 89.3 g of phenyl isocyanate are then added all at once at 10°-15° C., followed by 0.4 g of Dabco ®. The reaction mixture is then treated as described in Example 14.

About 7 g of a colourless crystalline product, melting point 205° C., showing the typical IR absorption bands of hydantoin are obtained by recrystallization. Analysis calculated on the basis of 1,3-diphenyl-5-(N-phenylaminocarbonyl methyl)-hydantoin gives the following results:

| Calculated: | C 71.7 | H 5.0 | N 10.9 |
|---|---|---|---|
| Found: | C 71.5 | H — | N 10.6 |

I claim:

1. A process for the preparation of a poly(thio)hydantoin, which comprises reacting an organic isocyanate or isothiocyanate having two or more isocyanate or isothiocyanate moieties with an unsaturated dicarboxylic acid of the formula:

$$\text{HOOC}-\underset{\underset{R_1}{|}}{C}=\underset{\underset{R_2}{|}}{C}-\text{COOH}$$

at a temperature of from −20° C. to +500° C., wherein $R_1$ and $R_2$ are hydrogen, halogen, substituted or unsubstituted aliphatic, aliphatic-aromatic, aromatic or heterocyclic.

2. A process as claimed in claim 1, wherein the isocyanate or isothiocyanate corresponds to the formula:

$$R_3(NCQ)_n$$

wherein $R_3$ is as substituted or unsubstituted aliphatic, aliphatic-aromatic, aromatic, or heterocyclic, n is the valency of $R_3$ and is an integer of from 2 to 4, and Q is oxygen or sulphur.

3. A process as claimed in claim 1, wherein $R_1$, $R_2$ and $R_3$ are the same or different and are hydrogen, halogen, an aliphatic $C_1$–$C_{20}$ group, an aliphatic-aromatic $C_7$–$C_{20}$ group, an aromatic $C_6$–$C_{20}$ group or a heterocyclic group with 5 to 16 ring members and at least one N, O, or S atom in the ring and $R_3$ represents an alkyl group with 2 to 20 C-Atoms, all of which may be substituted, $C_1$–$C_{10}$ alkyl groups and/or $C_6$–$C_{12}$; an aryl group with 5 to 12 C-atoms; a cycloalkyl group with 5 to 12 C-atoms; and alkyl aryl group with 6 to 20 C-atoms; and an aryl or cycloalkyl group with 5 to 12 C-atoms containing hereto atoms such as N, O or S, with halogen or with aryl groups.

4. A process as claimed in claim 1, wherein at least 2 vals of isocyanate or isothiocyanate are reacted per mole of unsaturated dicarboxylic acid.

5. A process as claimed in claim 4, wherein 3 to 6 Vals of iso(thio)cyanate are reacted per mole of unsaturated dicarboxylic acid.

6. A process as claimed in claim 1, wherein the unsaturated dicarboxylic acid is maleic acid and/or fumaric acid.

* * * * *